United States Patent [19]

Wu et al.

[11] 4,234,752

[45] Nov. 18, 1980

[54] DEHYDRATION OF ALCOHOLS

[75] Inventors: Yulin Wu; Stanley J. Marwil, both of Bartlesville, Okla.

[73] Assignee: Phillips Petroleum Company, Bartlesville, Okla.

[21] Appl. No.: 79,744

[22] Filed: Sep. 28, 1979

[51] Int. Cl.$^3$ .............................................. C07C 1/27
[52] U.S. Cl. ...................................................... 585/640
[58] Field of Search ........................................ 585/640

[56] References Cited

U.S. PATENT DOCUMENTS

| | | | |
|---|---|---|---|
| 1,909,356 | 5/1933 | Jaeger | 585/640 |
| 2,297,062 | 9/1942 | McKee | 62/175.5 |
| 2,377,026 | 5/1945 | Miller | 585/640 |
| 2,636,057 | 4/1953 | Cutcher et al. | 585/640 |
| 2,786,802 | 3/1957 | Hanisian et al. | 585/652 |
| 2,949,493 | 8/1960 | Happel et al. | 585/640 |
| 3,600,455 | 8/1971 | Dean | 585/640 |

OTHER PUBLICATIONS

Natarajan et al., Indian Journal of Technology, vol. 10, No. 12, (Dec. 1972), pp. 463-464.

*Primary Examiner*—C. Davis

[57] ABSTRACT

An alcohol which can be straight chain or branch-chain and can contain from 2 to about 20 carbon atoms per molecule is dehydrated in the presence of gamma-alumina, which may be base-treated, employing an inert carrier gas. 3-Methyl-1-butanol was dehydrated over gamma-alumina employing nitrogen as the carrier gas to obtain yields well in excess of 90 percent with correspondingly high selectivities. 3-Methyl-1-butene having a 97.7 weight percent purity was obtained with base-treated gamma-alumina.

6 Claims, No Drawings

DEHYDRATION OF ALCOHOLS

BRIEF SUMMARY OF THE INVENTION

Alcohols are converted to olefins by dehydration over gamma-alumina in the presence of an inert carrier gas. Straight and branched chain alcohols having 2 to about 20 carbon atoms per molecule are converted.

DETAILED DESCRIPTION OF THE INVENTION

This invention relates to the production of olefins. It also relates to the dehydration of alcohols. In one of its aspects the invention provides a process for the dehydration of an alcohol to produce an olefin. In another of its aspects the invention provides an improved process for the dehydration of an alcohol to produce an olefin.

In one of its concepts the invention provides a process for the dehydration of an alochol which comprises contacting said alcohol in the presence of an inert carrier gas with gamma-alumina. In another of its concepts it provides a process for the dehydration of an alcohol to an olefin in the presence of gamma-alumina which has been treated with an activity-altering agent to obtain a surface activity, i.e., a surface on which excess acidic sites have been neutralized. In a further concept the invention provides a process as described herein wherein a temperature is employed at which the desired dehydration reaction will occur. In a still further concept of the invention, it provides such a process in which external cooling as a temperature control can be practiced.

The dehydration of alcohols to produce olefins is known. Principally, the reaction is one involving the removal of the elements of water from the alcohol. In some cases a single olefin will result upon the dehydration; in others, a mixture of olefins will be obtained.

It is desirable to have a process in which a minimum of isomerization, i.e., double-bond isomerization or skeletal isomerization, will occur. Ordinarily, isomerization yields to undesired products at the expense of desired ones when the dehydration of alcohols as here-described is effected.

It is an object of this invention to produce an olefin. It is another object of this invention to dehydrate an alcohol to produce an olefin. It is a further object of this invention to produce olefins from an alcohol with minimum double-bond isomerization. It is a further object of this invention to provide a process for the dehydration of an alcohol to an olefin which is desired and to produce said olefin in high yield and with a high conversion of the starting alcohol to the desired product.

Other aspects, concepts, objects and the several advantages of the invention are apparent from a study of this disclosure and the appended claims.

According to the present invention an alcohol is dehydrated over gamma-alumina in the presence of an inert carrier gas.

Alcohols which are dehydrated to the corresponding olefins by means of this invention generally include the straight chain or branched-chain alcohols containing from 2 to about 20 carbon atoms per molecule. These can contain primary, secondary, or tertiary alcohol groups. This invention yields especially beneficial results with branched-chain alcohols containing from 4 to about 10 carbon atoms.

Alcohols which can be used in the process of this invention include ethanol, n-propanol, 2-methyl-2-propanol, 3-methyl-1-butanol, 3-methyl-2-butanol, 2,4-dimethyl-1-hexanol, n-octanol, 2,11-dimethyl-2-dodecanol, n-hexadecanol, n-eicosanol, and the like. Mixtures of alcohols can be processed.

The olefins produced by the process of this invention correspond to the starting alcohol from which elements of water have been removed. In some cases, a single olefin will result in the dehydration step; in others a mixture of several possible olefins resulting from dehydration will be produced. This invention minimizes isomerization, i.e., double-bond isomerization or skeletal isomerization which converts desired products to now undesired products.

The inert carrier gas employed in this invention can be any gas, or any inert gas, which is unreactive at existing reaction conditions, such as nitrogen, helium, argon, and the like, or mixtures thereof.

It is preferable to employ the desirable alcohol and inert carrier gas in the absence of any additional solvent or diluent. It is within the scope of this invention to employ any solvent in the dehydration reaction which will not adversely affect the reaction.

The catalyst, gamma-alumina, is well-known and readily available commerically. Since the surface activity of gamma-alumina available from some sources can be different from that of others, it may be desirable to treat the gamma-alumina with a suitable activity-altering agent to obtain a catalyst with the desired surface activity. For example, if excess acidic sites are available on the alumina surface, excessive isomerization of desired product to undesired product may result. Acidic sites on the alumina surface may be neutralized by treatment of the alumina with aqueous potassium hydroxide or aqueous sodium hydroxide, followed by washing with water and subsequent drying, or otherwise altered.

The alcohol generally is added to the reactor under desired reaction conditions at a rate of from about 0.1 to 20 weight hourly space velocity, and preferably 0.5 to 2 weight hourly space velocity.

The amount of inert carrier gas has not been found to be critical to obtain good results according to this invention. However, generally from about 0.1 to 1000 and preferably 0.5 to 300 liters inert carrier gas (measured at standard conditions) per kilogram of alcohol is useful in the practice of this invention.

This invention is especially well suited for continuous reaction in which the alcohol and inert carrier gas is continuously passed over a bed of gamma-alumina at the desired reaction conditions.

Generally, temperatures in the range of from about 200° to 500° C. are suitable for the desired dehydration reaction to occur. It is currently preferable, however, to employ temperatures in the range of 300°–450° C. Due to the exothermicity of the dehydration reaction, it may be desirable to provide external means of cooling for the desired temperature control.

The pressures under which the desired dehydration reaction will occur can vary widely, for example, from about 50 to about 3,500 kPa. It is generally preferable, however, to maintain some pressure and pressures in the range of 100–700 kPa are now contemplated as being desirable.

The reaction mixture can be separated readily into desired products, by-products, and unreacted starting materials using conventional methods such as solvent extraction, fractional distillation, fractional condensation, etc. An especially suitable means for isolating desired product involves the passage of gaseous reactor effluent into successively cooler zones, for example, 50° C. followed by 0° C. followed by −70° C. Most of the water and unreacted starting materials condense at the higher temperatures, while desired olefins are recovered at the lower temperatures.

EXAMPLE I

In the following inventive and comparative runs, 3-methyl-1-butanol was dehydrated over gamma-alumina in the presence or absence of nitrogen to produce 3-methyl-1-butene.

A tubular reactor of 46 cm length and 1 cm I.D. was packed with gamma-alumina (40 mesh, 24.8 gram). The reactor was heated at 350° C. and maintained at atmospheric pressure during the runs. The alcohol was introduced into the top of the column at 18.1–18.4 ml/hr. Inventive run 1 also employed nitrogen at a flow rate of 30 ml/min while comparative run 2 employed no nitrogen. The effluent from the reactor was passed successively through three separation zones, the first maintained at 50° C., the second at 0° C., and the third at −70° C. Analysis of the collected fractions by gas/liquid chromatography showed that the first collection zone contained primarily water while the lower temperature zones contained primarily 3-methyl-1-butene. The following table contains data calculated from feed rate, fraction weight, and fraction composition.

TABLE

| Run No. | $N_2$ | Yield,[1] % | Selectivity,[2] % | Conversion,[3] % |
|---|---|---|---|---|
| 1 (Inv.) | yes | 90 | 96.4 | 93.4 |
| 2 (Comp.) | no | 75.3 | 96.3 | 78.2 |

[1]Percentage of 3-methyl-1-butanol converted to 3-methyl-1-butene.
[2]Percentage of 3-methyl-1-butene in total products.
[3]Yield × 100/selectivity.

EXAMPLE II

The following inventive run illustrates the dehydration of 3-methyl-1-butanol to 3-methyl-1-butene over base-treated gamma-alumina in the presence of nitrogen.

Gamma-alumina was base-treated by mixing gamma-alumina (11.4 kg) and an aqueous solution containing 30 gm KOH in 7.6 liters water. After gently stirring the slurry for 30 minutes at room temperature, the liquid phase was drained and the solid phase was washed 3 times with distilled water. The thus-treated alumina was dried at 82° C. at reduced pressure with a nitrogen purge.

A tubular reactor 3.66 m by 7.6 cm I.D. was packed with 10 kg of base-treated gamma-alumina. The reactor was maintained at 350° C. and 310–350 kPa. Alcohol and nitrogen were added to the top of the column at a rate of 11.8 l/hr and 425 l/hr, (standard conditions), respectively. Reactor effluent was collected by condensation. Fractional distillation of condensate gave a fraction containing 3-methyl-1-butene in 97.7 weight percent purity. The gamma-alumina employed here was in the form of 1.6 mm diameter cylindrical extrudate.

Reasonable variation and modification are possible in the scope of the foregoing disclosure and the appended claims to the invention the essence of which is that an alcohol has been found to be readily dehydratable to obtain high yields and high conversion of starting material to product by employing, under reaction conditions as described, gamma-alumina and an inert carrier gas.

We claim:

1. A process for the conversion of an alcohol to an olefin which comprises subjecting said alcohol under dehydration reaction conditions of temperature and pressure to the presence of gamma-alumina in the presence of an inert carrier gas.

2. A process according to claim 1 wherein the gamma-alumina has been base-treated.

3. A process according to claim 1 wherein the alcohol is at least one alcohol selected from straight chain and branched-chain alcohols having from 2 to about 20 carbon atoms per molecule.

4. A process according to claim 1 wherein the alcohol is at least one of the following: ethanol, n-propanol, 2-methyl-2-propanol, 3-methyl-1-butanol, 3-methyl-2-butanol, 2,4-dimethyl-1-hexanol, n-octanol, 2,11-dimethyl-2-dodecanol, n-hexadecanol and n-eicosanol.

5. A process according to claim 1 wherein the reaction conditions include a temperature of from about 200° to about 500° C. and a pressure from about 50 to about 3500 kPa.

6. A process according to claim 1 wherein 3-methyl-1-butanol is dehydrated to produce 3-methyl-1-butene and nitrogen is the inert carrier gas.

* * * * *